United States Patent
Aldinger et al.

(10) Patent No.: US 9,975,920 B2
(45) Date of Patent: May 22, 2018

(54) PURIFICATION OF IMMUNOGLOBULINS FROM PLASMA

(71) Applicant: Merck Patent GmbH, Darmstadt (DE)

(72) Inventors: Annika Aldinger, Darmstadt (DE); Achim Schwaemmle, Rossdorf (DE); Matthias Joehnck, Muehltal (DE); Dirk Mueller, Mannheim (DE); Marc Mazur, Mannheim (DE)

(73) Assignee: MERCK PATENT GMBH, Darmstadt (DE)

( * ) Notice: Subject to any disclaimer, the term of this patent is extended or adjusted under 35 U.S.C. 154(b) by 239 days.

(21) Appl. No.: 14/821,886

(22) Filed: Aug. 10, 2015

(65) Prior Publication Data

US 2016/0046664 A1   Feb. 18, 2016

(30) Foreign Application Priority Data

Aug. 15, 2014  (EP) .................................... 14002852

(51) Int. Cl.
| | | |
|---|---|---|
| *B01D 41/00* | (2006.01) | |
| *C07K 1/18* | (2006.01) | |
| *B01J 20/26* | (2006.01) | |
| *B01J 20/285* | (2006.01) | |
| *B01D 15/36* | (2006.01) | |
| *B01J 41/14* | (2006.01) | |
| *B01J 41/20* | (2006.01) | |
| *B01D 61/00* | (2006.01) | |

(52) U.S. Cl.
CPC .............. *C07K 1/18* (2013.01); *B01D 15/363* (2013.01); *B01J 20/264* (2013.01); *B01J 20/265* (2013.01); *B01J 20/285* (2013.01); *B01J 41/14* (2013.01); *B01J 41/20* (2013.01)

(58) Field of Classification Search
CPC ........ B01D 15/08; B01D 15/26; B01D 15/36; B01D 15/361; B01D 37/00; B01D 43/00; B01D 61/00; B01D 69/02; B01D 71/00; B01D 71/52; B01J 41/00; B01J 41/04; B01J 41/12; B01J 41/09; B01J 47/00; B01J 47/014; B01J 47/12

USPC ..................... 210/638, 660, 681, 683, 500.21
See application file for complete search history.

(56) References Cited

U.S. PATENT DOCUMENTS

| | | | |
|---|---|---|---|
| 4,430,496 A * | 2/1984 | Abbott ..................... | B01J 41/10 210/198.2 |
| 4,675,384 A * | 6/1987 | Dromard .............. | C07K 14/765 210/263 |
| 5,453,186 A | 9/1995 | Muller et al. | |
| 5,759,404 A * | 6/1998 | Ericsson .............. | B01D 15/327 210/502.1 |
| 8,765,897 B2 | 7/2014 | Joehnck et al. | |
| 2011/0091727 A1 | 4/2011 | Joehnck et al. | |
| 2013/0046056 A1* | 2/2013 | Spector .............. | B01D 15/3809 525/54.1 |
| 2014/0155565 A1 | 6/2014 | Joehnck et al. | |

FOREIGN PATENT DOCUMENTS

| | | |
|---|---|---|
| EP | 0337144 A1 | 10/1989 |
| WO | 2007014591 A1 | 2/2007 |

OTHER PUBLICATIONS

Yan Yao et al. "Determination of pore size distributions of porous chromatographic adsorbents by inverse size-exclusion chromatography" Journal of Chromatography A, (2004), vol. 1037, pp. 273-282.
D. Gueffroy "Buffers—A Guide fro the Preparation and use of Buffers in Biological Systems" Calbiochem (1975), 37 pages.
Joseph Bertolini et al. "Production of Plasma Proteins for Therapeutic Use" John Wiley & Sons (2013).

* cited by examiner

*Primary Examiner* — Allison G Fitzsimmons
(74) *Attorney, Agent, or Firm* — Millen White Zelano and Branigan, PC; John Sopp

(57) ABSTRACT

The present invention relates to the purification of target molecules like immunoglobulins from plasma. The use of a certain type of ion exchanger based on a crosslinked polyvinylether results in especially high yields of the target molecule.

14 Claims, No Drawings

PURIFICATION OF IMMUNOGLOBULINS FROM PLASMA

The present invention relates to the purification of target molecules like immunoglobulins from plasma. The use of a certain type of ion exchanger based on a hydrophilic chemically stable polyvinylether resin results in especially high yields of the target molecule.

BACKGROUND OF THE INVENTION

Human and animal blood comprises many proteins and enzymes, which possess e.g. therapeutic properties. Some of these proteins may be found in the red blood cells whereas others are found in solution in plasma or serum. Such proteins are the target for large-scale and specific isolation with the aim of purifying and standardising the proteins for use as human therapeutic agents. Examples of prominent blood proteins that are isolated for therapeutic use: albumin, immunoglobulin G, Factor IX, Factor VIII and alpha-1-proteinase inhibitor. Some of these proteins are produced in the scale of several thousand kg per year (albumin and IgG) while others are produced only in the gram to kilogram per year scale. However, on a worldwide basis many million liters of blood per year are processed for the purpose of isolating these proteins.

Blood, blood plasma and blood serum are extremely complicated protein containing solutions that comprise many other types of compounds other than the protein(s) or enzyme(s) of interest. The isolation of specific target molecules from this type of sample requires sophisticated and often multi-step purification procedures.

One common problem with the current production methods of especially immunoglobulin G is the substantial loss of immunoglobulin G during the purification process, estimated to be at least 30% to 35% of the total IgG content of the starting material. One challenge is to maintain the quality of viral inactivation and lack of impurities which can cause adverse reactions, while enlarging the yield of IgG. At the current production levels of IgG, what may be considered small increases in the yield are in fact highly significant. Even a 2% increase in efficiency would generate a remarkable increase in yield and productivity.

As such, a need exists for improved and more efficient methods for manufacturing IgG products.

BRIEF DESCRIPTION OF THE INVENTION

It has been found that a certain type of chromatographic material or matrix can be very effectively used for the anion exchange purification of target molecules from plasma samples. The matrix is a hydrophilic polyvinylether carrying between 600 and 1200 μmol/g anionic groups. The target molecules can be obtained in very high yields and excellent purities.

The present invention is thus directed to a method for purifying a target molecule from a plasma sample by
a) Providing a plasma sample comprising the target molecule
b) subjecting said plasma sample to an ion exchange chromatography on a polyvinylether matrix carrying between 600 and 1200 μmol/g anionic groups whereby purified target molecule is eluted from the matrix.

In a preferred embodiment, the matrix is a copolymer formed by copolymerisation of at least one compound from the group a) and b) with a) at least one hydrophilically substituted alkyl vinyl ether of the formula I

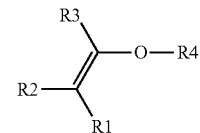

where R1, R2, R3, independently of one another, can be H or C1 to C6 alkyl, preferably H or —CH$_3$,
and R4 is a radical which carries at least one hydroxyl group and
b)
at least one crosslinking agent conforming to formula II and/or III and/or IV with

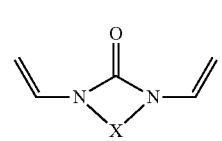

where X is a divalent alkyl radical having 2 to 5 C atoms, preferably 2 or 3 C atoms, in which one or more methylene groups which are not adjacent and are not located in the direct vicinity of N may be replaced by O, C=O, S, S=O, SO$_2$, NH, NOH or N and one or more H atoms of the methylene groups may be substituted, independently of one another, by hydroxyl groups, C1-C6-alkyl, halogen, NH$_2$, C5-C10-aryl, NH—(C1-C8)-alkyl, N—(C1-C8)-alkyl$_2$, C1-C6-alkoxy or C1-C6-alkyl-OH, and

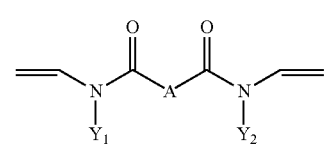

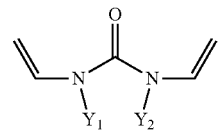

where Y1 and Y2 in formula III and IV are, independently of one another, C1 to C10 alkyl or cycloalkyl, where one or more non-adjacent methylene groups or methylene groups which are not located in the direct vicinity of N may be replaced by O, C=O, S, S=O, SO$_2$, NH, NOH or N and one or more H of the methylene groups may be substituted, independently of one another, by hydroxyl groups, C1-C6-alkyl, halogen, NH$_2$, C5-C10-aryl, NH(C1-C8)alkyl, N(C1-C8)alkyl$_2$, C1-C6-alkoxy or C1-C6-alkyl-OH,
or C6 to C18 aryl, where one or more H in the aryl system may be substituted, independently of one another, by hydroxyl groups, C1-C6-alkyl, halogen, NH$_2$, NH(C1-C8) alkyl, N(C1-C8)alkyl$_2$, C1-C6-alkoxy or C1-C6-alkyl-OH and
A is a divalent alkyl radical having 2 to 5 C atoms, preferably 2 or 3 C atoms, in which one or more non-adjacent methylene groups or methylene groups which are not located in the direct vicinity of N may be replaced by O, C=O, S, S=O, $SO_2$, NH, NOH or N and one or more H of the methylene groups may be substituted, independently of one another, by hydroxyl groups, C1-C6-alkyl, halogen, $NH_2$, C5-C10-aryl, NH(C1-C8)alkyl, N(C1-C8)alkyl$_2$, C1-C6-alkoxy or C1-C6-alkyl-OH.

R4 in formula I is typically an alkyl radical, a cycloaliphatic radical or an aryl radical which carries at least one hydroxyl group.

In a very preferred embodiment the matrix is formed by copolymerisation of a hydrophilically substituted alkyl vinyl ether employed selected from the group of 1,4-butanediol monovinyl ether, 1,5-pentanediol monovinyl ether, diethylene glycol monovinyl ether or cyclohexanedimethanol monovinyl ether and
divinylethyleneurea (1,3-divinylimidazolin-2-one) as crosslinking agent.

In a preferred embodiment, the ionic groups have been attached to the matrix by subjecting the polyvinylether matrix to cerium catalyzed graft polymerization. This is preferably performed according to U.S. Pat. No. 5,453,186 page 9 example 8, where preferably the charged group is the positively charged trimethylammoniumalkyl group.

In a preferred embodiment, the ion exchange group is a positively charged trimethylammoniumalkyl group.

In a preferred embodiment, the ion exchange chromatography is performed in the flow-through mode.

In a preferred embodiment, the target molecule is an immunoglobulin, preferably human immunoglobulin, most preferred human immunoglobulin G.

In another embodiment the target molecule is separated from IgA, IgM, albumin, transferrin and factor XIa.

In another embodiment, the matrix in step b) is eluted with a buffer having a pH between 4 and 7.4.

In one embodiment, the sample is applied to the matrix in an amount of 25 to 150 g of protein in the sample per liter matrix.

In a preferred embodiment, loading and elution of the matrix in step b) is performed with an acetate buffer comprising between 0.005 and 1 M acetate.

In one embodiment, the matrix is made of particles with average particle size diameters between 20 and 250 µm.

Pore sizes (e.g. pore radii) of the matrix refer to the pore sizes of the particles prior to the surface modification reaction and are being determined by inverse size exclusion chromatography. Procedures for determination are described in the literature (Journal of Chromatography A, Volume 1037, Issues 1-2, Pages 273-282).

In one embodiment the pore radii are between 30 to 150 nm.

In one embodiment after elution of the target molecule from the matrix in step b), in a subsequent step c) the matrix is eluted with a buffer having a pH below the pH of the buffer used in step b) whereby an IgM containing product is eluted from the matrix.

In one embodiment after elution of the target molecule from the matrix in step b), in a subsequent step c) the matrix is treated with a buffer having a pH below the pH of the buffer used in step b) whereby IgA, IgM, and factor XIa are eluted from the matrix.

DEFINITIONS

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a ligand" includes a plurality of ligands and reference to "an antibody" includes a plurality of antibodies and the like.

Unless defined otherwise, all technical and scientific terms used herein have the same meaning as commonly understood by one of ordinary skill in the art to which this invention is related. The following terms are defined for purposes of the invention as described herein.

As used herein the term "target molecule" refers to any molecule, substance or compound that shall be isolated, separated or purified from one or more other components, e.g. impurities, in a sample. Examples of target molecules are antibodies, fragment antigen binding (Fab), fragment constant region (Fc), proteins, peptides, recombinant proteins, other natural compounds. In a preferred embodiment, the target molecule is a protein. In a very preferred embodiment, the target molecule is an antibody. In an especially preferred embodiment the target molecule is an immunoglobulin. In the production and/or purification process the target molecule is typically present in a liquid. The liquid might be water, a buffer, a non-aqueous solvent like ethanol or any mixture thereof. Beside the target molecule said liquid may comprise one or more impurities. The composition of the liquid may change during production and/or purification depending on the process steps that are performed. After a chromatographic step the liquid typically comprises other solvents than before because of the eluent used in the chromatographic step. Typically only after the very last purification step the target molecule might be dried for preparing the final dosage form.

The term "antibody" refers to a protein which has the ability to specifically bind to an antigen. "Antibody" or "IgG" further refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively.

An exemplary immunoglobulin (antibody) structural unit is composed of two pairs of polypeptide chains, each pair having one "light" (about 25 kD) and one "heavy" chain (about 50-70 kD), said chains being stabilized, for example, by interchain disulfide bonds. The N-terminus of each chain defines a variable region of about 100 to 110 or more amino acids primarily responsible for antigen recognition. The terms variable light chain (V L) and variable heavy chain (V H) refer to these light and heavy chains respectively.

Antibodies may be monoclonal or polyclonal and may exist in monomeric or polymeric form, for example, IgM antibodies which exist in pentameric form and/or IgA antibodies which exist in monomeric, dimeric or multimeric form. Antibodies may also include multispecific antibodies (e.g., bispecific antibodies), and antibody fragments so long as they retain, or are modified to comprise, a ligand-specific binding domain. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. When produced recombinantly, fragments may be expressed alone or as part of a larger protein called a fusion protein. Exemplary fragments include Fab, Fab', F(ab')2, Fc and/or Fv fragments.

Exemplary fusion proteins include Fc fusion proteins. According to the present invention fusion proteins are also encompassed by the term "antibody".

In some embodiments, an antibody is an Fc region containing protein, e.g., an immunoglobulin. In some embodiments, an Fc region containing protein is a recombinant protein which includes the Fc region of an immunoglobulin fused to another polypeptide or a fragment thereof. Exemplary polypeptides include, e.g., renin; a growth hormone, including human growth hormone and bovine growth hormone; growth hormone releasing factor; parathyroid hormone; thyroid stimulating hormone; lipoproteins; α-1-antitrypsin; insulin α-chain; insulin β-chain; proinsulin; follicle stimulating hormone; calcitonin; luteinizing hormone; glucagon; clotting factors such as factor VIIIC, factor IX, tissue factor, and von Willebrand factor; anti-clotting factors such as Protein C; atrial natriuretic factor; lung surfactant; a plasminogen activator, such as urokinase or tissue-type plasminogen activator (t-PA); bombesin; thrombin; hemopoietic growth factor; tumor necrosis factor-α and -β; enkephalinase; RANTES (regulated on activation normally T-cell expressed and secreted); human macrophage inflammatory protein (MIP-1-α); a serum albumin such as human serum albumin; Muellerian-inhibiting substance; relaxin α-chain; relaxin β-chain; prorelaxin; mouse gonadotropin-associated peptide; a microbial protein, such as β-lactamase; DNase; IgE; a cytotoxic T-lymphocyte associated antigen (CTLA) (e.g., CTLA-4); inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as αFGF and βFGF; epidermal growth factor (EGF); transforming growth factor (TGF) such as TGF-alpha and TGF-β, including TGF-βI, TGF-β2, TGF-β3, TGF-β4, or TGF-β5; insulin-like growth factor-I and -II (IGF-I and IGF-II); des(I-3)-IGF-I (brain IGF-I), insulin-like growth factor binding proteins (IGFBPs); CD proteins such as CD3, CD4, CD8, CD 19 CD20, CD34, and CD40; erythropoietin; osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-I to IL-IO; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CDI Ia, CDI Ib, CDI Ic, CD 18, an ICAM, VLA-4 and VCAM; a tumor associated antigen such as HER2, HER3 or HER4 receptor; and fragments and/or variants of any of the above-listed polypeptides. In addition, an antibody according to the present invention is any protein or polypeptide, fragment or variant thereof, that binds specifically to any of the above-listed polypeptides.

As used herein, and unless stated otherwise, the term "sample" refers to any composition or mixture that contains a target molecule. Samples may be derived from biological or other sources. Biological sources include eukaryotic sources like animals or humans. Preferred samples are blood or plasma samples derived from mammalians. The sample may also include diluents, buffers, detergents, and contaminating species and the like that are found mixed with the target molecule. The sample may be "partially purified" (i.e., having been subjected to one or more purification steps, such as filtration or centrifugation steps) or may be obtained directly from an organism producing the target molecule. A plasma sample is any sample comprising plasma or parts of plasma.

The term "impurity" or "contaminant" as used herein, refers to any foreign or objectionable molecule, including a biological macromolecule such as DNA, RNA, one or more host cell proteins, nucleic acids, endotoxins, lipids, impurities of synthetic origin and one or more additives which may be present in a sample containing the target molecule that is being separated from one or more of the foreign or objectionable molecules. The term "impurity" or "contaminant" as used herein can also be applied to certain immunoglobulins which need to be separated from the target molecule like immunoglobulin A which causes allergic reactions in patents as well as immunoglobulin M. Additionally, such impurity may include any reagent which is used in a step of the production and/or purification process.

The terms "purifying," "separating," or "isolating," as used interchangeably herein, refer to increasing the degree of purity of a target molecule by separating it from a composition or sample comprising the target molecule and one or more other components, e.g. impurities. Typically, the degree of purity of the target molecule is increased by removing (completely or partially) at least one impurity from the composition.

The term "chromatography" refers to any kind of technique which separates an analyte of interest (e.g. a target molecule) from other molecules present in a mixture. Usually, the target molecule is separated from other molecules as a result of differences in rates at which the individual molecules of the mixture migrate through a stationary medium or matrix under the influence of a moving phase, or in bind and elute processes. Examples for chromatographic separation processes are reversed phase chromatography, ion exchange chromatography, size exclusion chromatography, affinity chromatography, hydrophobic interaction chromatography and mixed mode chromatography.

A "buffer" is a solution that resists changes in pH by the action of its acid-base conjugate components. Various buffers which can be employed depending, for example, on the desired pH of the buffer are described in Buffers. A Guide for the Preparation and Use of Buffers in Biological Systems, Gueffroy, D., ed. Calbiochem Corporation (1975). Non-limiting examples of buffers include MES, MOPS, MOPSO, Tris, HEPES, phosphate, acetate, citrate, succinate, and ammonium buffers, as well as combinations of these.

The term "matrix" or "chromatography matrix" are used interchangeably herein and refer to any kind of particulate sorbent, resin or solid phase which in a separation process separates a target molecule (e.g., an Fc region containing protein such as an immunoglobulin) from other molecules present in a mixture. Usually, the target molecule is separated from other molecules as a result of differences in rates at which the individual molecules of the mixture migrate through the matrix under the influence of a moving phase, or in bind and elute processes. The matrix consisting of resin particles can be put in columns or cartridges. Typically the matrix carries one or more types of ligands.

A "ligand" is a functional group that is attached to the chromatography matrix and that determines the binding properties of the matrix. Examples of "ligands" include, but are not limited to, ion exchange groups, hydrophobic interaction groups, hydrophilic interaction groups, thiophilic interactions groups, metal affinity groups, affinity groups, bioaffinity groups, and mixed mode groups (combinations of the aforementioned). Preferred ligands that can be used herein include, but are not limited to, are strong anion exchange groups, such as trimethylammonium chloride The term "ion-exchange" and "ion-exchange chromatography" refers to the chromatographic process in which a target molecule (e.g., an Fc region containing target protein) in a mixture interacts with a charged compound linked (such as by covalent attachment) to an ion exchange matrix such that the target molecule interacts non-specifically with the charged compound more or less than solute impurities or contaminants in the mixture. The impurities in the mixture elute from a column of the ion exchange material faster or slower than the target molecule or are bound to or excluded from the resin relative to the target molecule. "Ion-exchange chromatography" specifically includes cation exchange, anion exchange, and mixed mode ion exchange chromatography. Anion exchange chromatography can bind the target molecule (e.g., an Fc region containing target protein) followed by elution or can predominately bind the impurities while the target molecule "flows through" the column. Preferably, the anion exchange chromatography step is performed in a flow-through mode.

The phrase "ion exchange matrix" refers to a chromatography matrix that is negatively charged (i.e. a cation exchange resin) or positively charged (i.e. an anion exchange resin). The charge may be provided by attaching one or more charged ligands to the matrix, e.g. by covalent linking. Alternatively, or in addition, the charge may be an inherent property of the matrix.

The term "anion exchange matrix" is used herein to refer to a chromatography matrix which is positively charged, e.g. having one or more positively charged ligands, such as quaternary amino groups, attached thereto.

When "loading" a separation column in bind and elute mode, a buffer is used to load the sample or composition comprising the target molecule (e.g., an Fc region containing target protein) and one or more impurities onto a chromatography column (e.g an ion exchange column). The buffer has a conductivity and/or pH such that the target molecule is bound to the chromatography matrix while ideally all the impurities are not bound and flow through the column.

When "loading" a separation column to "flow through" a target molecule a buffer is used to load the sample or composition comprising the target molecule (e.g., an Fc region containing target protein) and one or more impurities onto a chromatography column (e.g. an ion exchange column). The buffer has a conductivity and/or pH such that the target molecule is not bound to the chromatography matrix and flows through the column while ideally all the impurities are bound the column.

Typically the buffer in which the sample is loaded on the matrix is called loading buffer or sample buffer.

The term "equilibrating" refers to the use of a buffer to equilibrate the chromatography matrix prior to loading the target molecule. Typically, the loading buffer is used for equilibrating.

By "wash" or "washing" a chromatography matrix is meant passing an appropriate liquid, e.g. a buffer through or over the matrix. Typically washing is used to remove weakly bound contaminants from the matrix prior to eluting the target molecule and/or to remove non-bound or weakly bound target molecule after loading.

In this case, typically, the wash buffer and the loading buffer are the same. In case virus inactivation buffer is used, it is used to inactivate certain present virus prior to eluting the target molecule. In this case, typically, the virus inactivation buffer differs from loading buffer since it may contain detergent/detergents or have different properties (pH/conductivity/salts and their amounts).

Washing can also be used to remove contaminants from the matrix after the elution of the target molecule. This is done by passing an appropriate liquid, e.g. a buffer through or over the matrix after the elution of the target molecule. In this case, typically, the washing buffer differs from loading buffer. It may contain detergent/detergents or have different properties (pH/conductivity/salts and their amounts). The washing buffer is for example an acidic buffer.

To "elute" a molecule (e.g., a polypeptide of interest like Immunoglobulin G or an impurity) from a chromatography matrix is meant to remove the molecule therefrom. Elution may take place directly in flow though mode when the target molecule is eluted with the solvent front of the loading buffer or by altering the solution conditions such that a buffer different from the loading buffer competes with the molecule of interest for the ligand sites on the chromatography resin. A non-limiting example is to elute a molecule from an ion exchange resin by altering the ionic strength of the buffer surrounding the ion exchange material such that the buffer competes with the molecule for the charged sites on the ion exchange material.

The term "average particle size diameter" or d50 means the average particle size distribution value at 50% of the cumulative particle size distribution. Particle size is determined by laser-diffraction, preferably with Malvern 'Master Sizer.

The term "average pore size" means the average pore size distribution value at 50% of the cumulative pore size distribution.

The terms "flow-through process," "flow-through mode," and "flow-through operation," as used interchangeably herein, refer to a separation technique in which at least one target molecule (e.g., an Fc-region containing protein or an antibody) contained in a sample along with one or more impurities is intended to flow through a chromatography matrix, which usually binds the one or more impurities, where the target molecule usually does not bind (i.e., flows through) and is eluted from the matrix with the loading buffer.

The terms "bind and elute mode" and "bind and elute process," as used herein, refer to a separation technique in which at least one target molecule contained in a sample (e.g., an Fc region containing protein) binds to a suitable chromatography matrix (e.g., an ion exchange chromatography media) and is subsequently eluted with a buffer different from the loading buffer.

DETAILED DESCRIPTION OF THE INVENTION

The starting material of the present purification process can be any sample comprising the target molecule to be purified. Typically the sample is or has been obtained from blood or plasma. Advantageously it is an immunoglobulin-containing plasma protein fraction. The starting material for this can be normal human plasma or may originate from donors with high titers of specific antibodies, e. g. hyperimmune plasma.

According to the method of the present invention such sample comprising the target molecule is subjected to at least one purification step in which the sample is loaded onto a chromatography matrix comprising anion exchange functionalities.

It has been found that the use of a certain type of chromatography matrix according to the present invention results in especially higher yields of 5-10% combined with higher purity of the target molecule compared to for example methacrylate copolymer based strong anion exchangers like Macro-Prep® High Q or sepharose based anion exchangers like Q Sepharose FF. E.g. compared to Q Sepharose FF the purity expressed as sum out of IgA and IgM in the IgG target fraction is typically 5 times higher, compared to Macro-Prep® High Q the yield of the target protein IgG is typically 7.7% higher, see Table 1 for reference.

This remarkable effect is achieved by using a hydrophilic polyvinylether matrix carrying between 600 and 1200 µmol/g anionic groups.

The matrix to be used is preferably based on a hydrophilic crosslinked polymer based on a copolymer at least comprising a) at least one hydrophilically substituted alkyl vinyl ether of the formula I

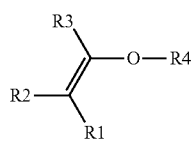

where R1, R2, R3, independently of one another, can be H or C1 to C6 alkyl, preferably H or —CH$_3$,
and R4 is a radical which carries at least one hydroxyl group
and
b)
at least one crosslinking agent conforming to formula II and/or III and/or IV with

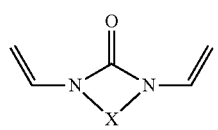

where X is a divalent alkyl radical having 2 to 5 C atoms, preferably 2 or 3 C atoms, in which one or more methylene groups which are not adjacent and are not located in the direct vicinity of N may be replaced by O, C=O, S, S=O, SO$_2$, NH, NOH or N and one or more H atoms of the methylene groups may be substituted, independently of one another, by hydroxyl groups, C1-C6-alkyl, halogen, NH$_2$, C5-C10-aryl, NH—(C1-C8)-alkyl, N—(C1-C8)-alkyl$_2$, C1-C6-alkoxy or C1-C6-alkyl-OH, and

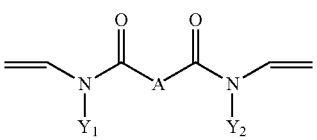

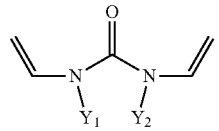

where Y1 and Y2 in formula III and IV are, independently of one another, C1 to C10 alkyl or cycloalkyl, where one or more non-adjacent methylene groups or methylene groups which are not located in the direct vicinity of N may be replaced by O, C=O, S, S=O, SO$_2$, NH, NOH or N and one or more H of the methylene groups may be substituted, independently of one another, by hydroxyl groups, C1-C6-alkyl, halogen, NH$_2$, C5-C10-aryl, NH(C1-C8)alkyl, N(C1-C8)alkyl$_2$, C1-C6-alkoxy or C1-C6-alkyl-OH, or C6 to C18 aryl, where one or more H in the aryl system may be substituted, independently of one another, by hydroxyl groups, C1-C6-alkyl, halogen, NH$_2$, NH(C1-C8)alkyl, N(C1-C8)alkyl$_2$, C1-C6-alkoxy or C1-C6-alkyl-OH
and A is a divalent alkyl radical having 2 to 5 C atoms, preferably 2 or 3 C atoms, in which one or more non-adjacent methylene groups or methylene groups which are not located in the direct vicinity of N may be replaced by O, C=O, S, S=O, SO$_2$, NH, NOH or N and one or more H of the methylene groups may be substituted, independently of one another, by hydroxyl groups, C1-C6-alkyl, halogen, NH$_2$, C5-C10-aryl, NH(C1-C8)alkyl, N(C1-C8)alkyl$_2$, C1-C6-alkoxy or C1-C6-alkyl-OH.

R4 in formula I is typically an alkyl radical, a cycloaliphatic radical or an aryl radical which carries at least one hydroxyl group.

This means the polymer is formed by copolymerisation of at least one compound from the group of the hydrophilically substituted alkyl vinyl ethers of the formula I and at least one compound from the group of the crosslinking agents of the formula II and/or III and/or IV. Preferably, only one compound from the group of the hydrophilically substituted alkyl vinyl ethers of the formula I and one compound from the group of the crosslinking agents of the formula II, III or IV is employed.

In a preferred embodiment, R4 in formula I is
a straight-chain or branched C1 to C10 alkyl radical, in which one or more non-adjacent methylene groups may be replaced by O, C=O, S, S=O, SO$_2$, NH, NOH, N and/or in which one or more H atoms may be substituted, independently of one another, by C1-C6-alkyl, C5-C10-aryl, halogen, NH$_2$, NH(C1-C8)alkyl, N(C1-C8)alkyl$_2$, C1-C6-alkoxy or C1-C6-alkyl-OH and in which at least one OH group is present either on the C1 to C10 alkyl radical or on a substituent, or a cycloaliphatic radical, typically having 5 to 10 C atoms, in which one or more non-adjacent methylene groups may be replaced by O, C=O, S, S=O, SO$_2$, NH, NOH, N and/or in which one or more H atoms of the cycloaliphatic radical may be substituted, independently of one another, by C1-C6-alkyl, C5-C10-aryl, halogen, NH$_2$, NH(C1-C8)alkyl, N(C1-C8)alkyl$_2$, C1-C6-alkoxy or C1-C6-alkyl-OH, where at least one OH group is present either on the cycloaliphatic ring or on a side chain or substituent, or a C6 to C18 aryl radical, where one or more H atoms in the aryl radical may be substituted, independently of one another, by hydroxyl groups, C1-C6-alkyl, C5-C10-aryl, halogen, $NH_2$, $NH(C1-C8)alkyl$, $N(C1-C8)alkyl_2$, C1-C6-alkoxy or C1-C6-alkyl-OH, where at least one OH group is present either on the aryl radical or on a side chain or substituent, or a C5 to C18 heteroaryl radical, where one or more H atoms in the heteroaryl radical may be substituted, independently of one another, by hydroxyl groups, C1-C6-alkyl, C5-C10-aryl, halogen, $NH_2$, $NH(C1-C8)alkyl$, $N(C1-C8)alkyl_2$, C1-C6-alkoxy or C1-C6-alkyl-OH, where at least one OH group is present either on the heteroaryl radical or on a side chain or substituent.

In a particularly preferred embodiment, R4 in formula I is a straight-chain or branched C1 to C10 alkyl radical, in which one or more non-adjacent methylene groups may be replaced by O, S, $SO_2$ or NH and/or in which one or more H atoms may be substituted, independently of one another, by C1-C6-alkyl, C5-C10-aryl, C1-C6-alkoxy or C1-C6-alkyl-OH and in which at least one OH group is present either on the C1 to C10 alkyl radical or on a substituent, or a cycloaliphatic radical, typically having 5 to 10 C atoms, in which one or more non-adjacent methylene groups may be replaced by O, S, $SO_2$ or NH and/or in which one or more H atoms of the cycloaliphatic radical may be substituted, independently of one another, by C1-C6-alkyl, C5-C10-aryl, C1-C6-alkoxy or C1-C6-alkyl-OH, where at least one OH group is present either on the cycloaliphatic ring or on a side chain or substituent, or a C6 to C14 aryl radical, where one or more H atoms in the aryl radical may be substituted, independently of one another, by hydroxyl groups, C1-C6-alkyl, C5-C10-aryl, C1-C6-alkoxy or C1-C6-alkyl-OH, where at least one OH group is present either on the aryl radical or on a side chain or substituent, or a C6 to C14 heteroaryl radical, in which at least one N atom is present as heteroatom and where one or more H atoms in the heteroaryl radical may be substituted, independently of one another, by hydroxyl groups, C1-C6-alkyl, C5-C10-aryl, C1-C6-alkoxy or C1-C6-alkyl-OH, where at least one OH group is present either on the heteroaryl radical or on a side chain or substituent.

In a preferred embodiment, the hydrophilically substituted alkyl vinyl ether employed is a compound of the formula I in which R4 is a radical which carries a hydroxyl group.

In a preferred embodiment, the hydrophilically substituted alkyl vinyl ether employed is 1,2-ethanediol monovinyl ether, 1,3-propanediol monovinyl ether, 1,4-butanediol monovinyl ether, 1,5-pentanediol monovinyl ether, 1,6-hexanediol monovinyl ether or diethylene glycol monovinyl ether and the cycloaliphatic vinyl ether employed is cyclohexanedimethanol monovinyl ether, particularly preferably 1,4-butanediol monovinyl ether, 1,5-pentanediol monovinyl ether, diethylene glycol monovinyl ether or cyclohexanedimethanol monovinyl ether.

The crosslinking agents employed are preferably compounds of the formula II. Preference is given to the use of divinylpropyleneurea (1,3-divinyl-tetra-hydropyrimidin-2-one) or particularly preferably divinylethyleneurea (1,3-divinylimidazolin-2-one).

The proportion of the hydrophilically substituted alkyl vinyl ethers with respect to the weight of the polymer is typically between 1% (by weight) and 90% (by weight) or a maximum proportion by weight of the alkyl vinyl ether which corresponds to a molar ratio of 2:1, based on a bifunctional crosslinking agent, if the alkyl vinyl ether does not homopolymerise. The proportion of the hydrophilically substituted alkyl vinyl ethers is preferably between 10 and 80% (% by weight), particularly preferably between 35 and 60%. Accordingly, the proportion of the crosslinking agent is between 10 and 99 (% by weight), preferably between 20 and 90%, particularly preferably between 40 and 65%.

In another preferred embodiment, the polymer is porous having pore sizes between 2 and 200 nm, more preferred between 30 and 150 nm In another embodiment, the polymer is in the form of particles having average particle size diameters diameter between 25 and 250 μm, most preferred between 30 to 90 μm.

The polymer carries ligands comprising an anion exchange group.

In a preferred embodiment, the polymer has been derivatised by means of structures which have been attached to the polymer by graft polymerisation.

In a preferred embodiment, the polymer has been derivatied by means of structures which have been attached to the polymer by graft polymerisation with cerium(IV) catalysis, preferrably according to U.S. Pat. No. 5,453,186 page 9 example 8, where preferably the charged group is the positively charged trimethylammoniumalkyl group.

Further details about the material to be used in the method of the present invention and about its production can be found in WO 2007/014591.

Ligands are known to the person skilled in the art in the area of chromatography. Ligands are substituents which can be introduced into the support material as early as during the synthesis of the base material or subsequently and influence the surface properties of the support material. In particular, targeted derivatisation of support materials by means of ligands produces support materials having certain chromatographic properties. In particular, ligands to be used in the present invention can have the following terminal groups: an ionic or ionisable group, for example —$NR^7R^8$ or —$NR^7R^8R^9$, in which $R^7$ and $R^8$, independently of one another, H, alkyl having 1-5 C atoms and $R^9$ alkyl having 1-5 C atoms with the proviso that, if X=—$NR^7R^8R^9$, $R^7$ and $R^8$ cannot be H, -guanidinium In a preferred embodiment the polymer to be used as a matrix in the method of the present invention is derivatised by graft polymerisation with tentacle-like structures, which can in turn carry the corresponding ligands or be functionalised by means of the latter. The grafting is preferably carried out in accordance with EP 0 337 144 page 12 example 8 or U.S. Pat. No. 5,453,186 page 9 example 8 using N-(2-Trimethylammoniumethyl)-acrylamide. The polymerisation catalyst employed is cerium(IV) ions, since this catalyst forms free-radical sites on the surface of the base material, from which the graft polymerisation of the monomers is initiated.

The polymerisation is terminated by termination reactions involving the cerium salts. For this reason, the (average) chain length can be influenced by the concentration ratios of the base material, the initiator and the monomers. Furthermore, uniform monomers or also mixtures of different monomers can be employed; in the latter case, grafted copolymers are formed.

Suitable monomers for the preparation of the graft polymers and further details about the grafting procedure are e.g.

disclosed in WO 2007/014591, EP 0337 144, especially page 12, example 8 and U.S. Pat. No. 5,453,186 page 9, example 8.

Preferably the matrix is derivatised with ionic groups by graft polymerisation whereby the resulting chains that are grafted onto the base polymer matrix have a length of between 2 and 100, preferably 5 and 60, in particular between 10 and 30 monomer units, each unit typically carrying one ionic group.

Preferred ionic groups are positively charged Trimethylammoniumethyl groups.

The matrix might carry additional other functional groups like hydrophobic or hydrophilic groups in addition to the anion exchange groups but in any case it has anion exchange groups.

The ionic capacity of the anion exchange matrix to be used in the present invention is typically between 600 and 1200 µmol/g, preferably between 700 and 1000 µmol/g, most preferred between 800 and 1000 µmol/g.

Suitable materials to be used in the method of the invention are Eshmuno® QPX and Eshmuno® QPX Hicap from Merck KGaA, Germany. Those resins comprise polyvinylether beads synthesized according to the procedure disclosed in WO 2007/014591, to which polymer structures are grafted utilizing grafting techniques according to EP 0337 144 page 12 example 8 and U.S. Pat. No. 5,453,186 page 9 example 8 and yielding surface polymer structures carrying positively charged trimethylammoniumethyl groups, where the charge density in the case of Eshmuno QPX and Eshmuno QPX Hicap resins is adjusted to 600 to 1200 µmol/g.

For performing the method of the present invention, the sample is subjected to an anion exchange chromatography whereby the chromatography matrix is a hydrophilic polyvinylether functionalized with anionic groups as described above.

The sample is preferably a pre-purified plasma sample comprising immunoglobulin G, preferably 75 to 99% by weight of IgG. The samples comprise preferably at least 80% by weight, more preferred at least 85% by weight, especially preferred more than 90% by weight most preferred between 92 and 98% by weight of immunoglobulin G. "% by weight" is in this case related to the mass of the dried plasma sample.

Before applying the sample to the matrix, the matrix can be washed and/or equilibrated.

Washing can be done with a moderately acidic pH 4.0-5.5 buffer like acetate buffer, optionally with salt, for example NaCl. The buffer typically has a concentration between 200 and 1000 mM/l.

Equilibration is done with an equilibration buffer with a pH between 4 and 7.4. Preferably the pH of the equilibration buffer is the same as the pH of the sample. The concentration of the equilibration buffer is typically in the range of 0.005 to 2 Mol/l, preferably in the range of 0.005 to 0.05 Mol/l.

Equilibration buffer is typically identical to the sample buffer.

Prior to washing and/or equilibrating the matrix with the equilibration buffer it is possible to treat the matrix with a basic aqueous liquid having a pH of more than 10, preferably around 14. Such a treatment is known to a person skilled in the art. It is suitable to remove potential impurities from the matrix. Suitable liquids are aqueous sodium hydroxide or aqueous potassium hydroxide. The basic aqueous liquid can be removed from the matrix directly with the equilibration buffer or with a slightly acidic aqueous washing buffer like acetic acid buffer, preferably in a e.g. acetate concentration between 200 to 1000 mM/l.

The sample is typically applied to the chromatography matrix in a buffer (also called loading buffer or sample buffer). The buffer preferably has a pH between 4.0 and 7.4. Suitable buffers are carbonic acid/silicate buffer, acetic acid buffers, citrate buffers, phosphate buffers, glycine buffers and/or 2-(N-morpholino)ethanesulfonic acid (MES) buffers. Most preferred is an acetate buffer.

The buffers are typically used in concentrations between 5 and 500 mmol/l, preferably between 5 and 100 mmol/l, most preferred between 5 and 50 mmol/l.

The IgG concentration in the sample feed is typically adjusted to between 1 to 50 g/l.

The amount of sample to be loaded on the matrix is variable in a wide range.

The matrix can be loaded with very small amounts of the sample, like e.g. 10 g sample per 1 liter of matrix volume. It is also possible to load up to 150 g sample per liter of matrix volume. Preferably more than 25 g/l matrix volume are loaded, most preferred between 25 and 100 g/l.

The chromatographic purification of the sample can be performed in the bind-and-elute mode or preferably in the flow-through mode. In the flow-through mode, the target molecule is essentially not bound or adsorbed to the matrix. That means the target molecule moves through the matrix essentially with the solvent front—i.e. the front of the loading buffer—and is recovered from the matrix essentially together with the solvent front. It has been found that when using the matrix according to the present invention in the flow-through mode, the target molecule can be typically eluted from the matrix with the 5-fold, preferably the three-fold, very preferred the two-fold volume of eluent with regard to the volume of the matrix. The eluent is in this case identical with the loading buffer. The impurities are retained on the matrix. With the flow-through mode at least 80%, preferably more than 90%, most preferred more than 95% of the target molecule can be recovered from the matrix.

It has been further found that the binding of the impurities to the matrix is very stable as long as the matrix is eluted with the loading buffer. This offers the possibility to also enlarge the volume of the loading buffer used for elution of the target molecule to more than the 5-fold volume of the matrix, if necessary, so that the target molecule can be eluted nearly complete (about 97% yield) while its purity is still very high (typically >99.5%).

The method of the present invention performed in the flow-through mode is especially suitable to separate immunoglobulin G as target molecule from impurities like IgA, IgM, albumin and Serine Proteases like factor XIa.

But it is also suitable for the isolation of an IgM containing product or for the isolation of IgA, IgM and/or factor XIa. It has been found that when performing the chromatographic purification in the flow-through mode, immunoglobulin G is eluted essentially with the solvent front. After elution of IgG, the elution buffer (which for the elution of IgG is identical to the loading buffer) can be changed to support elution of further secondary target molecules like IgA, IgM and factor XIa. For example the secondary target molecules may be a mixture of IgA and IgM. For this, the acidity of the elution buffer is typically increased. Preferably the elution buffer for this application has a pH between 4 and 5.5 whereby the pH is in any case lower than the pH of the loading buffer. Typically the pH of the buffer used to elute IgA, IgM and/or factor XIa is between 0.5 and 2 pH units below the pH of the loading buffer.

Consequently, the method of the present invention not only allows to purify one target molecule, like for example IgG, but also two or more target molecules, like IgG as well as IgA, IgM and/or factor XIa, for example IgG as well as a mixture of IgA and IgM.

The method of the present invention can be used as a single, separate purification step but it can also preferably be combined with other purification steps that are performed prior or after the method of the invention.

The preferred target molecule to be purified with the method of the invention is IgG. Known procedures for the purification of IgG typically comprise several steps including precipitation, filtration and chromatographic steps. Such methods are for example disclosed in "Production of Plasma Proteins for Therapeutic Use", edited by J. Bertolini, N. Goss, J. Curling; John Wiley and sons Inc., 2013., see e.g. chapter 13.

The method of the present invention can favorably be applied to substitute one or more of the purification steps of the known methods.

Preferably, the crude plasma sample is first subjected to a precipitation step in which a major proportion of the non-IgG-proteins, especially those of higher molecular weight, the aggregated immunoglobulins and other aggregated proteins as well as potentially infectious particles precipitate without substantial precipitation of monomeric IgG. This can for example be achieved by ethanol precipitation yielding IgG enriched intermediates called fraction I+II+III or fraction II+III or fraction II. Following acid precipitation and filtration steps, the feed for the anion exchange chromatography can be obtained.

It is also possible to perform additional chromatographic steps.

Following anion chromatography the purified IgG is typically being nanofiltered and formulated.

Unexpectedly, it has been found that the use of the certain type of chromatographic matrix not only offers the possibility to purify target molecules like IgG very effectively with yields >95% by simple flow-through ion exchange chromatography, it also ensures the separation of IgG from IgA below 25 mg/L, IgM below 25 mg/L, albumin (below detection limit) and factor XIa (below detection limit). The very good separation of IgG from these substances can further be used to additionally isolate one or more of those substances in also very good purity and yield.

The purity and yield that can be achieved with the chromatographic matrix to be used according to the present invention is better compared to equivalent anion exchange steps on different matrices. While known procedures often combine an anion exchange purification step with a successive cation exchange polishing step, such a polishing step is typically not needed when the anion exchange purification is performed according to the present invention.

The entire disclosures of all applications, patents, and publications cited above and below, as well as of corresponding EP 14002852.3, filed Aug. 15, 2014, are hereby incorporated by reference.

EXAMPLES

Example 1—Purification of IgG

The chromatographic matrix (Eshmuno® QPX Hicap, Merck KGaA) is equilibrated with 500 mM acetate buffer (pH 6.5) and subsequently treated with 25 mM Acetate buffer (pH 6.5). The sample is a solution comprising 15 g/l IgG with the following impurities: IgA (1000 mg/l) and IgM (500 mg/l) and factor XIa (50 pM/l) in 25 mM acetate buffer (pH 6.5).

The sample is applied to the matrix equivalent to a protein loading of 75 g/l of the matrix at 130 cm/h. The matrix is then eluted with 25 mM acetate buffer, pH 6.5 until IgG is completely eluted from the matrix. IgG is recovered in more than 95% yield, whereby the purified IgG comprises less than 25 mg/l IgM and IgA. The amount of factor XIa can be reduced to 0.0 pM. IgM and IgA can be further obtained from the matrix in a purity of more than 95% and with a yield of more than 95% by elution with an acidic buffer (300 mM Acetate buffer, pH 4.5). All steps run at 130 cm/h linear velocity.

Example 2—Purification of IgG on Various Matrices

General procedure:
Feed composition: 20 g/l IgG und 1 g/l IgA und 1 g/l IgM in 25 mM acetat pH 6.5.
Pre-Equilibration: 500 mM acetate buffer, pH 6.5
Equilibration: 25 mM acetate buffer, pH 6.5
Loading/Elution: 25 mM acetate buffer, pH 6.5
Flow Rate: >130 cm/h
Loading: 5 g/L (sum of IgM and IgA)
Wash: 250 mM acetate buffer, pH 4.5
Table 1 shows the yield, purity (concentration of impurities) and recovery data.

TABLE 1

|  | Eshmuno® QPX Hicap | Fractogel® EMD TMAE (M) | Macro-Prep® High Q | Q Sepharose FF |
|---|---|---|---|---|
| Yield IgG [%] | 95.7 ± 2.1 | 85-90 | 85-91 | 88 |
| Recovery IgG [%] | 101 ± 2 | 100 | 97 | 95 |
| IgA@10% [mg/L] | 9.1 ± 2.2 | 14 | 4 | >40 |
| IgM@10% [mg/L] | 34.0 ± 2.3 | 30 | 26 | >150 |
| IgG 4 [%] | >1.7 | <1.3 | <1.3 | n.d. |
| Factor XIa [ng/mL] | <0.001 | n.d. | 0.11 | n.d. |
| Albumin [%] | <0.1% | n.d. | <0.1% | n.d. |
| Experiments | 5 | 2 | 2 | 1 |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European Application No. EP 14002852.3, filed Aug. 15, 2014 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for purifying a target molecule from a plasma sample comprising:
   a) providing a plasma sample comprising the target molecule
   b) subjecting said plasma sample to an ion exchange chromatography on a polyvinylether matrix carrying between 600 and 1200 µmol/g anion exchange groups whereby purified target molecule is eluted from the matrix wherein the polyvinylether matrix is a copolymer obtained by copolymerisation of at least one compound from the group a) and one compound from group b) with
   a) being at least one hydrophilically substituted alkyl vinyl ether of the formula I

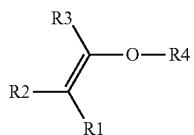

where R1, R2, R3, independently of one another, are H or C1 to C6 alkyl,
and R4 is a radical which carries at least one hydroxyl group and
   b) being at least one crosslinking agent of formula II, formula III or formula IV:

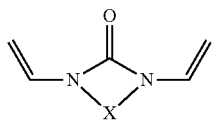

where X is a divalent alkyl radical having 2 to 5 C atoms in which one or more methylene groups which are not adjacent and are not located in the direct vicinity of N may be replaced by O, C=O, S, S=O, SO₂, NH, NOH or N and one or more H atoms of the methylene groups may be substituted, independently of one another, by hydroxyl groups, C1-C6-alkyl, halogen, NH₂, C5-C10-aryl, NH—(C1-C8)-alkyl, N—(C1-C8)-alkyl₂, C1-C6-alkoxy or C1-C6-alkyl-OH, and

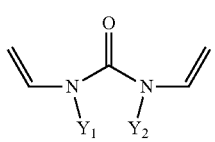

where Y1 and Y2 in formula III and IV are, independently of one another:
C1 to C10 alkyl or cycloalkyl, where one or more non-adjacent methylene groups or methylene groups which are not located in the direct vicinity of N may be replaced by O, C=O, S, S=O, SO₂, NH, NOH or N and one or more H of the methylene groups may be substituted, independently of one another, by hydroxyl groups, C1-C6-alkyl, halogen, NH₂, C5-C10-aryl, NH(C1-C8)alkyl, N(C1-C8)alkyl₂, C1-C6-alkoxy or C1-C6-alkyl-OH;
or C6 to C18 aryl, where one or more H in the aryl system may be substituted, independently of one another, by hydroxyl groups, C1-C6-alkyl, halogen, NH₂, NH(C1-C8)alkyl, N(C1-C8)alkyl₂, C1-C6-alkoxy or C1-C6-alkyl-OH; and
A is a divalent alkyl radical having 2 to 5 C atoms, in which one or mom non-adjacent methylene groups or methylene groups which are not located in the direct vicinity of N may be replaced by O, C=O, S, S=O, SO₂, NH, NOH or N and one or more H of the methylene groups may be substituted, independently of one another, by hydroxyl groups, C1-C6-alkyl, halogen, NH₂, C5-C10-aryl, NH(C1-C8)alkyl, N(C1-C8)alkyl₂, C1-C6-alkoxy or C1-C6-alkyl-OH.

2. Method according to claim 1, wherein the polyvinylether matrix is a copolymer obtained by copolymerisation of a hydrophilically substituted alkyl vinyl ether selected from: 1,4-butanediol monovinyl ether, 1,5-pentanediol monovinyl ether, diethylene glycol monovinyl ether or cyclohexanedimethanol monovinyl ether; and divinylethyleneurea (1,3-divinylimidazolin-2-one) as crosslinking agent.

3. Method according to claim 1, wherein the anion exchange groups have been attached to the matrix by subjecting the polyvinylether matrix to cerium catalyzed graft polymerization.

4. Method according to claim 1, wherein the polyvinylether matrix carries 700 to 1100 µmol/g of positively charged anion exchange groups which are graft polymerized to the matrix.

5. Method according to claim 1, wherein the anion exchange groups comprise trimethylammoniumalkyl groups.

6. Method according to claim 1, wherein the ion exchange chromatography is performed in a flow-through mode.

7. Method according to claim 1, wherein the target molecule is an immunoglobulin.

8. Method according to claim 1, wherein the target molecule is IgG and IgG is separated from IgA, IgM, albumin, and factor XIa in the plasma sample.

9. Method according to claim 1, wherein the matrix in the ion exchange chromatography step b) is eluted with a buffer having a pH between 4 and 7.4.

10. Method according to claim 1, wherein the plasma sample comprises protein and plasma sample is applied to the matrix in an amount such that there are 25 to 150 g of protein in the plasma sample per liter of the matrix.

11. Method according to claim 1, wherein loading and elution of the matrix in the ion exchange chromatography step b) is performed with an acetate buffer comprising between 0.005 and 1 M acetate.

12. Method according to claim 1, wherein the matrix is made of polyvinylether particles with an average particle size diameter of between 20 and 250 µm.

13. Method according to claim 1, wherein, after elution of the target molecule from the matrix with a buffer, in a subsequent step c) the matrix is eluted again with a buffer having a pH below the pH of the buffer used in step b) whereby in step c) IgA, IgM and factor XIa are eluted from the matrix.

14. The method of claim 2, wherein:
in formula II, X is a divalent alkyl radical having 2 to 3 C atoms, in which one or more methylene groups which are not adjacent and are not located in the direct vicinity of N may be replaced by O, C=O, S, S=O, SO$_2$, NH, NOH or N and one or more H atoms of the methylene groups may be substituted, independently of one another, by hydroxyl groups, C1-C6-alkyl, halogen, NH$_2$, C5-C10-aryl, NH—(C1-C8)-alkyl, N—(C1-C8)-alkyl$_2$, C1-C6-alkoxy or C1-C6-alkyl-OH, and in formula III, A is a divalent alkyl radical having 2 to 3 C atoms, in which one or more non-adjacent methylene groups or methylene groups which are not located in the direct vicinity of N may be replaced by O, C=O, S, S=O, SO$_2$, NH, NOH or N and one or more H of the methylene groups may be substituted, independently of one another, by hydroxyl groups, C1-C6-alkyl, halogen, NH$_2$, C5-C10-aryl, NH(C1-C8)alkyl, N(C1-C8)alkyl$_2$, C1-C6-alkoxy or C1-C6-alkyl-OH.

* * * * *

UNITED STATES PATENT AND TRADEMARK OFFICE
CERTIFICATE OF CORRECTION

PATENT NO. : 9,975,920 B2
APPLICATION NO. : 14/821886
DATED : May 22, 2018
INVENTOR(S) : Annika Aldinger Page 1 of 1

It is certified that error appears in the above-identified patent and that said Letters Patent is hereby corrected as shown below:

In the Claims

Column 18, Line 11 reads: "which one or mom non-adjacent methylene groups" should read --which one or more non-adjacent methylene groups--.

Column 18, Line 64 reads: "14. The method of claim 2, wherein" should read --14. The method of claim 1, wherein--.

Signed and Sealed this
Nineteenth Day of March, 2019

Andrei Iancu
*Director of the United States Patent and Trademark Office*